United States Patent
Zielinski et al.

(10) Patent No.: US 10,197,581 B2
(45) Date of Patent: *Feb. 5, 2019

(54) VITAMIN D ASSAYS

(71) Applicant: Enzo Life Sciences, Inc., Farmingdale, NY (US)

(72) Inventors: John F. Zielinski, Whitemore Lake, MI (US); Rory J. Olson, Rochester, MN (US); Michael C. Mullenix, Saline, MI (US)

(73) Assignee: Enzo Life Sciences, Inc., Farmingdale, NY (US)

( * ) Notice: Subject to any disclaimer, the term of this patent is extended or adjusted under 35 U.S.C. 154(b) by 163 days.

This patent is subject to a terminal disclaimer.

(21) Appl. No.: 15/254,017

(22) Filed: Sep. 1, 2016

(65) Prior Publication Data

US 2016/0370387 A1  Dec. 22, 2016

Related U.S. Application Data

(63) Continuation of application No. 14/772,098, filed as application No. PCT/US2014/020600 on Mar. 5, 2014, now Pat. No. 9,476,873, which is a continuation of application No. 13/826,747, filed on Mar. 14, 2013, now abandoned.

(51) Int. Cl.
   *G01N 33/82* (2006.01)
   *G01N 33/53* (2006.01)

(52) U.S. Cl.
   CPC ......... *G01N 33/82* (2013.01); *G01N 33/5308* (2013.01)

(58) Field of Classification Search
   CPC ........................... G01N 33/82; G01N 33/5308
   See application file for complete search history.

(56) References Cited

U.S. PATENT DOCUMENTS

| | | | |
|---|---|---|---|
| 4,081,525 | A | 3/1978 | Knight et al. |
| 4,585,862 | A | 4/1986 | Wang et al. |
| 7,087,395 | B1 | 8/2006 | Garrity et al. |
| 8,003,400 | B2 | 8/2011 | Kobold et al. |
| 2004/0096900 | A1 | 5/2004 | Laurie et al. |
| 2004/0132104 | A1 | 7/2004 | Sackrison et al. |
| 2005/0070015 | A1 | 3/2005 | Nakamura et al. |
| 2009/0093445 | A1 | 4/2009 | Kyriatsoulis et al. |
| 2009/0311316 | A1 | 12/2009 | Bishop et al. |
| 2010/0068725 | A1 | 3/2010 | Armbruster et al. |
| 2010/0285603 | A1 | 11/2010 | Kobold et al. |

FOREIGN PATENT DOCUMENTS

| | | | |
|---|---|---|---|
| EP | 1835290 | 9/2007 | |
| EP | 1931711 | 4/2009 | |
| WO | WO2002/057797 | 7/2002 | |
| WO | WO2003/023391 | 3/2003 | |
| WO | WO2007/039194 | 4/2007 | |
| WO | WO2007/083345 | 7/2007 | |
| WO | WO2009/017425 | 2/2009 | |
| WO | WO-2009138296 A2 * | 11/2009 | ............ B01D 53/90 |
| WO | WO2012/162165 | 11/2012 | |
| WO | WO2014/158864 | 10/2014 | |

OTHER PUBLICATIONS

Berns et al., "Prognostic Value of TP63 Protein Accumulation in Human Primary Breast Cancer: An Analysis by Luminomelric Immunoassay on 1491 Tumor Cytosis," *Anticancer Research*, vol. 17, pp. 3003-3006 (1997).
International Search Report and Written Opinion of copending application PCT/US14/20600, 13 pages.
Blomberg et al., Terbium and rhodamine as labels in a homogenous time-resolved fluorometric energy transfer assay of the beta subunit of human chorionic gonadotropin in serum, Clinical Chemistry 1999, 855-861, 45(6).
Charlton and Porter, Isolation of anti-hapten specific antibody fragments from combinatorial libraries, Methods in Molecular Biology 2002, 159-171, 178.
Dusso et al., Vitamin D, Am J Physiol Renal Physiol, 2005, F8-F28, 289.
Ersfeld et al., Analytical and clinical validation of the 25 OH vitamin D assay for the LIAISON automated analyzer, Clinical Biochemistry 2004, 867-874, 37.
Heijboer et al., Accuracy of 6 routine 25-hydroxyvitamin D assays: Influence of vitamin D binding protein concentration, Clinical Chemistry 2012, 543-548, 58(3).
Mayilo et al., Competitive homogenous digoxigenin immunoassay based on fluorescence quenching by gold nanoparticies, Analytica Chimica Acta 2009, 119-122, 646.
O'Beirne and Cooper, Heterogeneous enzyme immunoassay, The Journal of Histochemistry and Cytochemistry 1979, 1148-1162, 27(8).
Singh et al., C-3 epimers can account for a significant proportion of total circulating 25-hydroxyvitamin D in Infants, complicating accurate measurement and interpretation of vitamin D status, The Journal of Clinical Endocrinology & Metabolism 2006, 3055-3061, 91(8).
Winter et al., Making Antibodies by Phage Display Technology, Annu. Rev. Immunol. 1994, 433-455, 12.
Wong et al., Reproducibility and correlations of multiplex cytokine levels in asymptomatic persons, Cancer Epidermiol Biomarkers Prev 2008, 3450-3056, 17(12).

* cited by examiner

*Primary Examiner* — Andrea S Grossman
(74) *Attorney, Agent, or Firm* — Paul Diamond, Esq.

(57) ABSTRACT

The disclosure relates to methods for measuring levels of 25(OH)vitamin D (25OHD) in a mammalian fluid sample. The disclosure further relates to kits for measuring levels of 25(OH)vitamin D (25OHD) in a mammalian fluid.

27 Claims, 8 Drawing Sheets

VITAMIN D ASSAYS

1. CROSS-REFERENCE TO RELATED APPLICATIONS

This application is a continuation of U.S. application Ser. No. 14/772,098, filed Sep. 2, 2015, which is a 371 National Stage of PCT Application No. PCT/US2014/020600, filed Mar. 5, 2014, which is a continuation of U.S. application Ser. No. 13/826,747, filed Mar. 14, 2013, now abandoned, all of which are hereby incorporated by reference in their entirety.

2. BACKGROUND

The present disclosure generally relates to assays for vitamin D metabolites. More specifically, assays are provided that utilize reagents that adequately release the metabolite 25(OH)vitamin $D_2$ and 25(OH)vitamin $D_3$ from vitamin D binding protein (DBP), where the release reagents are identified that do not interfere with the assay.

Assays for metabolically active vitamin D in samples such as mammalian fluids (including milk, whole blood, serum and plasma) generally measure quantities of both 25(OH)vitamin $D_2$ ($25OHD_2$) and 25(OH)vitamin $D_3$ ($25OHD_3$) (collectively, 25OHD). $25OHD_2$ is metabolically converted from vitamin $D_2$ that is found in foods, and $25OHD_3$ is metabolically converted from vitamin $D_3$ that is present in some foods and the result of photolytic conversion of 7-dehydrocholesterol by sunlight (Dusso et al. 2005. Vitamin D. Am J Physiol Renal Physiol 289:F8; U.S. Pat. No. 8,003,400; U.S. Pat. No. 7,087,395). These 25OHD assays generally utilize chromatographic procedures since most immunoassays, when not preceded by laborious extraction and reconstitution procedures, have inaccuracies that are dependent on the DBP concentration (Heijboer et al. 2012. Clin. Chem. 58: 543-548). Furthermore, reagents that release 25OHD from DBP ("release reagents") can interfere with immunoassays but not chromatographic procedures (U.S. Pat. No. 8,003,400).

In humans, the DBP circulates at a 20-100 fold greater molar excess as compared to 25OHD (Dusso 2005). Because of this ratio, an effective immunoassay protocol must not simply be able to dissociate bound 25OHD from DBP but must also block the remaining available DBP so the analyte is not re-bound, an endpoint whose difficulty is magnified due to DBP having the greatest affinity towards the 25(OH) metabolite of vitamin D. In addition, reagents that release 25OHD from DBP will also act to release 25OHD from other proteins, such a 25OHD-specific antibody utilized in an immunoassay. Also, vitamin D is by nature a hydrophobic molecule so therefore once it is freed from DBP it must be in an environment in which it will remain free and therefore available for detection in the immunoassay. As such, a reagent used to dissociate bound 25OHD from DBP ("dissociation buffer") in an immunoassay must provide for the release of the majority of the sample 25OHD from DBP such that the 25OHD is available for binding to the anti-25OHD antibody while not interfering with the binding of 25OHD to the specific antibody utilized in the immunoassay.

There is, therefore, a need for an immunoassay that overcomes the above obstacles to provide a simplified, more rapid and more accurate assay than previous assays for 25OHD.

3. SUMMARY

In some embodiments, the present disclosure relates to a method of measuring 25(OH)vitamin D (25OHD) in a mammalian fluid sample comprising the steps of (a) contacting a sample containing 25OHD with an antibody that specifically binds to 25OHD in the presence of a release reagent; and (b) measuring the amount of 25OHD bound to the antibody.

In particular embodiments, the release reagent comprises at least one major release reagent selected from 1-butyl-4-methylpyridinium chloride and 1-ethyl-3-methylpyridinium ethyl sulfate, and at least one minor release reagent selected from methyl β-cyclodextrin and sodium salicylate.

In other embodiments, the disclosure relates to a method of measuring 25(OH)vitamin D (25OHD) in a mammalian fluid sample comprising the steps of (a) contacting a sample comprising 25OHD with a dissociation buffer comprising a release reagent selected from 1-butyl-4-methylpyridinium chloride, 1-ethyl-3-methylpyridinium ethyl sulfate and a mixture of 1-butyl-4-methylpyridinium chloride and 1-ethyl-3-methylpyridinium ethyl sulfate in a well of a microtiter plate; (b) contacting the mixture of step (a) with (i) add-in 25OHD bound to an enzyme and an antibody that specifically binds to 25OHD; (c) washing the well to remove add-in 25OHD that is not specifically bound; (d) adding a substrate of said enzyme bound to add-in 25OHD; (e) quantitatively measuring the signal produced by the reaction of substrate and enzyme in the well; and (f) comparing the measured signal with a standard curve of measurements of the product with known quantities of $25OHD_3$, $25OHD_2$ or a mixture thereof, to determine the amount of 25OHD in the sample.

The present disclosure further relates to a kit for measuring 25(OH)vitamin D (25OHD) in a mammalian fluid sample comprising an antibody that specifically binds to 25OHD, and a dissociation buffer comprising a release reagent selected from 1-butyl-4-methylpyridinium chloride, 1-ethyl-3-methylpyridinium ethyl sulfate, and a mixture thereof.

It should be noted that the indefinite articles "a" and "an" and the definite article "the" are used in the present application to mean one or more unless the context clearly dictates otherwise. Further, the term "or" is used in the present application to mean the disjunctive "or" or the conjunctive "and."

All publications mentioned in this specification are herein incorporated by reference. Any discussion of documents, acts, materials, devices, articles or the like that has been included in this specification is solely for the purpose of providing a context for the present disclosure. It is not to be taken as an admission that any or all of these matters form part of the prior art or were common general knowledge in the field relevant to the present disclosure as it existed anywhere before the priority date of this application.

The features and advantages of the disclosure will become further apparent from the following detailed description of embodiments thereof.

4. BRIEF DESCRIPTION OF THE FIGURES

FIG. 1 shows a decrease in pH of a dissociation buffer containing 1-butyl-4-methylpyridinium tetrafluoroborate over a nine-day period.

FIG. 2 shows the results of an experiment testing the effects of various concentrations of 1-butyl-4-methylpyridinium chloride on release of bound $25OHD_3$ from DBP. Data shown are for two serum samples with concentrations of $25OHD_3$ of 20 and 40 ng/mL. Percent inhibition by released 25OHD reflects the percentage difference from a sample containing no 25OHD.

FIG. 3 shows the results of an experiment testing the effects of various concentrations of 1-ethyl-3-methylpyridinium ethyl sulfate on release of bound 25OHD$_3$. Data shown are for two serum samples with concentrations of 25OHD$_3$ of 20 and 40 ng/mL. Percent inhibition by released 25OHD reflects the percentage difference from a sample containing no 25OHD.

FIG. 4 shows a graph comparing expected additive results versus experimental data for release of 25OHD$_3$ in the presence of a combination of various percentages of 1-butyl-4-methylpyridinium chloride and 15% 1-ethyl-3-methylpyridinium ethyl sulfate. Data shown are for the 40 ng/mL serum sample. Percent inhibition by released 25OHD reflects the percentage difference from a sample containing no 25OHD.

5. DETAILED DESCRIPTION

Figure 1:
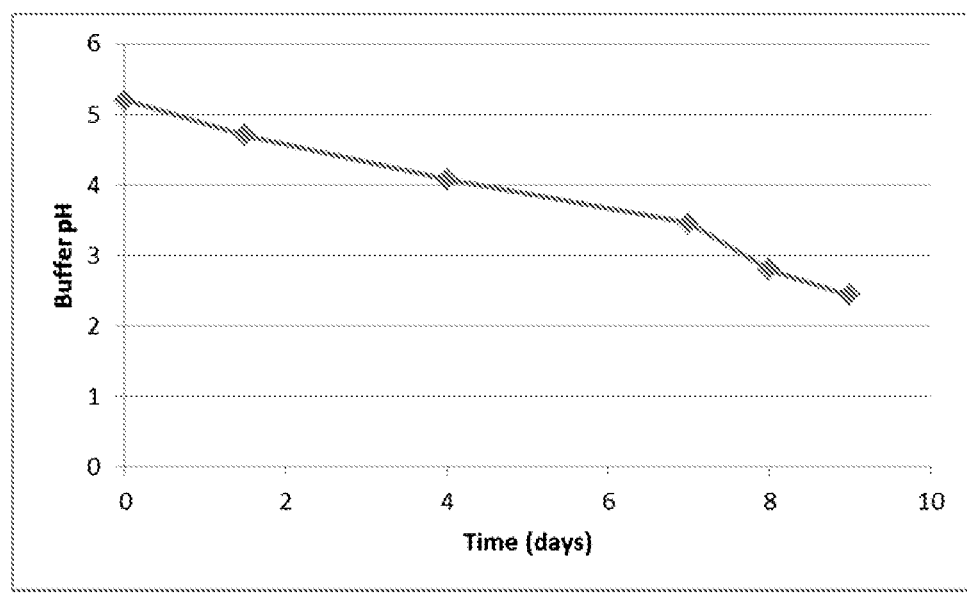

The inventors have identified compositions and methods for quantitation of 25OHD in mammalian fluids. In certain embodiments, the quantitation of 25OHD is by immunoassay. The compositions and methods overcome interference and simplify sample preparation with reagents that are used in chromatographic procedures to quantify 25OHD.

In one embodiment, the present disclosure provides a method for measuring the amount of 25OHD in a mammalian fluid sample, which comprises contacting a mammalian fluid sample with an antibody that specifically binds to 25OHD in the presence of a release reagent; and measuring the amount of 25OHD in the sample. In certain embodiments, the amount of 25OHD is measured by mass spectrometry.

The disclosure provides optimized conditions for measuring (i.e., quantifying) 25OHD in mammalian fluids by immunoassay. The invention is based in part on the discovery that release reagents utilized for chromatographic procedures that measure 25OHD are not suitable for immunoassay because they interfere with binding of 25OHD to a 25OHD-specific antibody or are unstable under immunoassay conditions. In particular, the inventors have discovered that 1-butyl-4-methylpyridinium tetrafluoroborate, while effective as a release reagent is unstable in buffer solutions and interferes with immunoassays. The inventors have further discovered that two related reagents, 1-butyl-4-methylpyridinium chloride and 1-ethyl-3-methylpyridinium ethyl sulfate are stable and effective release reagents suitable for immunoassay formats.

Accordingly, in one aspect, the present disclosure provides a method of measuring 25OHD in a sample comprising (i) contacting a sample containing 25OHD$_2$ and/or 25OHD$_3$ with an antibody that specifically binds to 25OHD$_2$ and/or 25OHD$_3$ in the presence of at least one release reagent; and (ii) quantitatively measuring the amount of 25OHD$_2$ and/or 23OHD$_3$ bound to the antibody.

In another aspect, the present disclosure provides a composition for measuring 25OHD$_2$ and/or 25OHD$_3$ in a sample comprising (i) an antibody that specifically binds to 25OHD$_2$ and/or 25OHD$_3$ and (ii) a dissociation buffer comprising at least one release reagent.

In certain embodiments, the present disclosure provides an immunoassay for measuring 25(OH)vitamin D ("25OHD") in a sample of a mammalian fluid. The immunoassay uses reagents comprising (a) an antibody that specifically binds to 25OHD and (b) a dissociation buffer that comprises 1-butyl-4-methylpyridinium chloride, 1-ethyl-3-methylpyridinium ethyl sulfate, or both 1-butyl-4-methylpyridinium chloride and 1-ethyl-3-methylpyridinium ethyl sulfate.

As used herein, the term "release reagent" is a compound, or a mixture of compounds, that aids the dissociation of vitamin D from vitamin D binding protein. In certain embodiments, the release reagent comprises a "major release reagent". In other embodiments, the release reagent comprises a "major release reagent" and a "minor release reagent". As used herein, a "major release reagent" is a compound or mixture of compounds that effects the dissociation of vitamin D from vitamin D binding protein, and a "minor release reagent" aids the dissociation process by, e.g., sequestering interfering compounds or solubilizing dissociated 25OHD.

As used herein, an antibody that "specifically binds" to 25OHD refers to an antibody that binds 25OHD in the epitope binding region (i.e., the variable region). In certain embodiments, an antibody employed in the assays of the present disclosure binds 25OHD$_2$. In other embodiments, the antibody binds 25OHD$_3$. In still other embodiments, the antibody binds to both 25OHD$_2$ and 25OHD$_3$. Typically, an antibody useful in the methods described herein binds to 25OHD$_2$ and/or 25OHD$_3$ with an affinity that is greater than the affinity of vitamin D binding protein for 25OHD$_2$ and/or 25OHD$_3$ under the assay conditions.

In some embodiments, the dissociation buffer comprises both 1-butyl-4-methylpyridinium chloride and 1-ethyl-3-methylpyridinium ethyl sulfate. In additional embodiments, the dissociation buffer further comprises methyl β-cyclodextrin and sodium salicylate. Without being bound to any particular function, it is believed that the 1-butyl-4-methylpyridinium chloride and 1-ethyl-3-methylpyridinium ethyl sulfate effect the release of 25OHD from DBP, the methyl β-cyclodextrin sequesters other matrix components that would interfere in the assay by reuptake of dissociated 25OHD, and the sodium salicylate aids in the solubilization of dissociated 25OHD. As used herein, 1-butyl-4-methylpyridinium chloride and 1-ethyl-3-methylpyridinium ethyl sulfate are major release reagents and methyl β-cyclodextrin and sodium salicylate are minor release reagents.

The sample to be tested in the methods of the invention can be from any mammal. In some embodiments, the sample is from a human, e.g., a human without any apparent disease, or a human that has, or is suspected of having, inadequate or excessive vitamin D levels. The immunoassay can be utilized to measure 25OHD in any mammalian fluid, including but not limited to serum, plasma, whole blood, milk, cerebrospinal fluid, sweat, bile, or an extract of any tissue or cell.

The methods described herein can utilize any antibody that specifically binds to 25OHD, including polyclonal or monoclonal antibodies, phage display-derived antibodies, chimeric antibodies, humanized antibodies, and antigen binding fragments of antibodies, including, e.g., Fab', F(ab')$_2$, Fab, Fv, rIgG, and scFv fragments. Moreover, unless otherwise indicated, the term "monoclonal antibody" is meant to include both intact molecules, as well as, antibody fragments (such as, for example, Fab and F(ab')$_2$ fragments) which are capable of specifically binding to 25OHD. Examples of useful antibodies are described in European Patent No. 1 931 711. The antibodies can be immunoglobulins of any vertebrate species, e.g., rabbit, goat, mouse, sheep, chicken, etc. Additionally, they can be from any source, e.g., from the serum of an animal injected with an immunogen such as any of the immunogens described above, or they can be produced from culture or ascites according to methods known in the art of hybridoma technology. Alternatively, the antibodies can be from recombinant sources, e.g., as described in Winter et al., 1994, Ann. Rev. Immunol. 12:433-55, or Charlton and Porter, 2002, Meth. Mol. Biol. 178:159-71. In some preferred embodiments, the antibody is a monoclonal antibody that specifically binds to both 25OHD$_2$ and 25OHD$_3$.

In certain embodiments, the methods described herein can utilize a "secondary antibody" that binds to an antibody that binds to 25OHD. Such secondary antibodies include polyclonal or monoclonal antibodies, phage display-derived antibodies, chimeric antibodies, humanized antibodies, and antigen binding fragments of antibodies, including, e.g., Fab', F(ab')$_2$, Fab, Fv, rIgG, and scFv fragments. Moreover, the secondary antibody can be an intact monoclonal antibody or an antibody fragment (such as, for example, Fab and F(ab')$_2$ fragments) which are capable of specifically binding to the anti-25OHD antibody. The secondary antibodies can be immunoglobulins of any vertebrate species and can be from any source, as discussed above for the anti-25OHD antibodies.

The methods provided here can have any format known in the art. In some embodiments, the method is performed in a liquid phase. In other embodiments, the method is performed on a surface, e.g., a bead (which can be, for example, silver or gold, fluorescent labeled, magnetic, plastic, glass or nitrocellulose), a nanoparticle, a slide or a microplate, for example a 96-well microplate. The surface can be made from any material that is stable under the conditions of the assay, for example, glass, plastic, nitrocellulose, PVDF, and the like. Non-limiting examples of immunoassay formats that can be used in the methods described herein are a radioimmunoassay (see, e.g., U.S. Pat. No. 4,081,525), a Luminex® assay (see, e.g., Wong et al., 2008, Cancer Epidemiol. Biomarkers 17:3450-6), a microarray assay, a fluorescence polarization immunoassay (see, e.g., U.S. Pat. No. 4,585,862), an immunoassay comprising a Förster resonance energy transfer (FRET) signaling system (see, e.g., Blomberg et al., 1999, Clin. Chem. 45:855-61; Mayilo et al., 2009, Analytica Chimica Acta 646:119-22), and enzyme immunoassay (a.k.a. enzyme linked immunosorbent assay [ELISA]). As is well known in the art, in ELISA an enzyme in combination with a substrate that becomes colored upon reaction with the enzyme provides the signal to quantify the antigen in the sample. See, e.g., O'Beirne and Cooper, 1979, J. Histochem. Cytochem. 27:1148-62.

TABLE 1

Summary of various immunoassay formats that can be utilized for detection of 25OHD. The general features of these assays are known in the art.

| Detection Method | 25OHD probe | Antibody | Other components |
|---|---|---|---|
| Scintillation proximity assay | Radio-iodinated | Immobilized | Scintillant-coated plate or bead |
| Fluorescence polarization assay | Fluorescently-labeled | Unlabeled | |
| Homogeneous time-resolved fluorescence assay | Allophyocyanin-labeled | Europium cryptate-labeled | |
| Amplified luminescence assay (ALPHAScreen) | Biotin-labeled | Acceptor bead-labeled | Streptavidin-labeled donor bead |
| Enzyme complementation assay | Inactive enzyme donor-labeled | Immobilized | Enzyme acceptor, enzyme substrate (e.g. fluorogenic β-galactosidase substrate) |
| Electrochemiluminescence assay | Ruthenium-labeled | Immobilized | Carbon electrode plates, chemical substrate and electrical stimulation |

Any immunoassay format known in the art for quantifying a hapten (a molecule that is too small to illicit an antibody immune response by itself) such as 25OHD can be utilized in the methods of the present disclosure. In certain embodiments, immunoassays for detection and quantification of haptens generally utilize a competitive format, i.e., where the hapten (here, 25OHD) in the sample competes with a labeled hapten (e.g., an enzyme bound to a hapten) which does not come from the sample ("add-in" hapten) for anti-hapten antibody binding sites such that fewer labeled hapten molecules are bound when there is a higher concentration of hapten in the sample. As used herein, the term "bound" includes both covalent binding (referred to as "conjugation") and non-covalent binding of one moiety, e.g., a hapten to another moiety, e.g., an enzyme or other labeling moiety. A "conjugate" refers to moieties (e.g., hapten and label) that are covalently bound. Thus, in these competitive assays, an increasing concentration of hapten in the sample results in fewer labeled hapten molecules bound to the solid phase, resulting in less signal measured. The signal can be generated in any way known in the art, for example an enzyme, as utilized in enzyme-linked immunosorbent assay (ELISA) or an analogous assay using a fluorescent label, which can be bound to a hapten. In such competitive assays, as defined herein, the sample can be added together with the labeled hapten to compete directly for antibody binding sites, or the sample and labeled hapten can be added sequentially such that the labeled hapten binds where the sample hapten is not bound.

In some embodiments, the immunoassay is a direct competitive ELISA, defined herein as where the 25OHD hapten is directly bound to an enzyme, or an indirect competitive ELISA, where the enzyme is bound to another molecule, e.g., a second antibody, or streptavidin.

In various embodiments, the method is an ELISA assay. In these embodiments, the ELISA assay can take any format known in the art. In some embodiments, 25OHD (e.g., 25OHD-BSA or 25OHD-polylysine) is bound to a solid phase. In these assays, the 25OHD-binding antibody is added with the sample. Here, the 25OHD in the sample competes with the solid phase-bound 25OHD for antibody binding sites such that fewer antibody molecules bind to the solid phase when there is more 25OHD in the sample. After washing, the amount of 25OHD antibody bound to the solid phase is measured, e.g., by utilizing in the competitive step a 25OHD antibody bound to an enzyme, or by adding a second antibody bound to an enzyme that binds to the bound 25OHD antibody. A number of assay designs for this configuration will be known to one of skill in the art.

In other embodiments, the 25OHD-binding antibody is bound to the solid phase, either directly or indirectly, the latter being where the solid phase is coated with a secondary antibody (for example goat or donkey antibodies that bind to mouse, rabbit or sheep monoclonal or polyclonal antibodies to 25OHD). In these assays, the sample and a labeled hapten are added to the solid phase to compete with antibody binding sites on the coated solid phase. After washing, a signal is generated, which measures the amount of labeled hapten that is bound to the solid phase. A number of assay designs for this configuration can be devised without undue experimentation.

Thus, in some embodiments, the immunoassay is performed on a microtiter plate coated with a coating antibody. In particular embodiments, the coating antibody is a polyclonal secondary antibody that specifically binds to the monoclonal antibody.

In some embodiments, the immunoassay is an enzyme-linked immunosorbent assay (ELISA) further comprising (a) incubating 25OHD bound to an enzyme with (i) an antibody that specifically binds to 25OHD and (ii) a mammalian fluid sample in a well of a microtiter plate;

(b) washing the well sufficiently to remove the 25OHD that is not specifically bound to the well;

(c) adding a substrate to the enzyme, wherein the product of the substrate reaction with the enzyme is measured spectrophotometrically;

(d) quantitatively measuring the product of the substrate reaction with the enzyme; and (e) comparing the measured product with a standard curve of measurements of the product with known quantities of $25OHD_3$ or $25OHD_2$ or both $25OHD_3$ and $25OHD_2$ to determine the amount of 25OHD in the sample.

In some embodiments of this ELISA assay, the coating antibody is a secondary antibody that specifically binds to the antibody that specifically binds to 25OHD. In other aspects, the coating antibody is the antibody that specifically binds to 25OHD.

In other embodiments, a method of measuring 25OHD in a mammalian fluid sample by ELISA is provided. The method comprises (a) combining the fluid with a dissociation buffer comprising at least one release reagent that dissociates 25OHD from vitamin D binding protein in the fluid wherein the release reagent is 1-butyl-4-methylpyridinium chloride or 1-ethyl-3-methylpyridinium ethyl sulfate;

(b) incubating 25OHD bound to an enzyme with (i) an antibody that specifically binds to 25OHD and (ii) the fluid combined with the dissociation buffer in a well of a microtiter plate;

(c) washing the well sufficiently to remove enzyme bound 25OHD that is not specifically bound to the well;

(d) adding a substrate to the enzyme, wherein the product of the substrate reaction with the enzyme is measured spectrophotometrically;

(e) quantitatively measuring the product of the substrate reaction with the enzyme; and (f) comparing the measured product with a standard curve of measurements of the product with known quantities of $25OHD_3$ or $25OHD_2$ or both $25OHD_3$ and $25OHD_2$ to determine the amount of 25OHD in the sample.

In various embodiments of these methods, the dissociation buffer comprises more than one release reagent, for example both 1-butyl-4-methylpyridinium chloride and 1-ethyl-3-methylpyridinium ethyl sulfate. In other embodiments, the dissociation buffer further comprises methyl β-cyclodextrin and/or sodium salicylate.

As with the immunoassay discussed above, this method can utilize any antibody that specifically binds to 25OHD, including any polyclonal, monoclonal or phage display-derived antibody. Also like the immunoassay discussed above, this method may be performed with any mammalian fluid sample. In particular embodiments, 25OHD levels in human serum or plasma are measured.

In some embodiments, the methods provided herewith are performed on a microtiter plate coated with a coating antibody, for example a secondary antibody that specifically binds to an antibody that specifically binds to 25OHD. A non-limiting example of such a coating antibody, is ImmunoReagents' affinity purified donkey anti-sheep IgG. Alternatively, in other embodiments, the methods are performed on a microtiter plate having wells that are coated with the antibody that specifically binds to 25OHD.

In additional embodiments, a kit for measuring 25OHD in a mammalian fluid by immunoassay is provided. The kit comprises (a) an antibody that specifically binds to 25OHD and (b) a dissociation buffer comprising at least one release reagent that dissociates 25OHD from vitamin D binding protein in the fluid, wherein the release reagent is 1-butyl-4-methylpyridinium chloride or 1-ethyl-3-methylpyridinium ethyl sulfate.

In various aspects of these kits, the dissociation buffer comprises both 1-butyl-4-methylpyridinium chloride and 1-ethyl-3-methylpyridinium ethyl sulfate. The dissociation buffer can also further comprise methyl β-cyclodextrin and/or sodium salicylate.

These kits can also further comprise any other reagent utilized in the immunoassay or methods discussed above. These may include a microtiter plate with a well that is coated with an antibody. In some embodiments, the well of the microtiter plate is coated with a secondary antibody that specifically binds to the antibody that specifically binds to 25OHD. In other embodiments, the well of the microtiter plate is coated with an antibody that specifically binds to 25OHD. The kits can further comprise an enzyme bound to 25OHD. In some embodiments, the enzyme is covalently bound to 25OHD. In other embodiments, the enzyme is non-covalently bound to 25OHD. In some embodiments, the 25OHD is modified at the hydroxyl group with a linking group and the enzyme is covalently bound to 25OHD via the linking group. The enzyme can be any enzyme whose presence can be detected by the addition of a substrate that the enzyme converts to a detectable product. Non-limiting examples include alkaline phosphatase, horseradish peroxidase, and luciferase. In other embodiments, the 25OHD is bound to a non-enzymatic compound that is itself detectable, e.g., a fluorescent dye or chemiluminescent compound, or can be detected by binding to a labeled binding partner, e.g., biotin, avidin or streptavidin. Suitable reactive groups for covalently binding 25OHD to enzymes or other compounds include, for example, N-hydroxysuccinimide, aryl azide, carbodimide, hydrazide, hydroxymethyl phosphine, imidoesters, isocyanate, maleimide, NHS, PFP, psoralen, pyridyl disulfide, and vinyl sulfone.

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

6. EXAMPLES

6.1. Example 1: Screening of ELISA Conditions for Detecting 25OHD ELISA Protocol ELISA for 25OHD was performed according to the following protocol. Wells of a polystyrene microtiter plate were coated with an affinity purified donkey anti-sheep IgG coating antibody (ImmunoReagents, Inc., Raleigh N.C.) that specifically binds to an antibody that specifically binds to both 25OHD$_2$ and 25OHD$_3$. 90 µL of dissociation buffer were added to each well of the coated plate. 10 µL of a serum sample, discrete standard or serum diluent (for NBS and Bo wells) were added to wells containing dissociation buffer. Wells were incubated for approximately 5 minutes at room temperature with shaking, after which 50 µL of conjugate diluent were added to NSB wells. 100× conjugate concentrate was diluted 1:100 with supplied conjugate diluent, and 50 µL of the 1× conjugate was added to all assay plate wells. 50 µL of a sheep monoclonal anti-25OHD antibody (Bioventix) was added to all assay plate wells except for the NSB wells. Wells were incubated at room temperature with shaking for 60 minutes. 20× wash buffer concentrate was diluted 1:20 with distilled H$_2$O, and assay plate wells were washed 3 times with 400 µL of 1× wash buffer, aspirating between each wash. 200 µL of pNPP substrate were added to each well and wells were incubated at room temperature with shaking for 30 minutes. Absorbance at 405 nm wavelength was measured for each well.

In order to optimize the ELISA 25OHD assay, components of the dissociation buffer, the assay buffer and the wash buffer, and conditions for performing various steps in the protocol were tested in the assay. Various reagents were tested alone or in combination for their effects on dissociation of 25OHD from DBP. Tested reagents included: 1-butyl-4-methylpyridinium tetrafluoroborate, 1-butyl-3-methylimidazolium tetrafluoroborate, 1-butyl-4-methylpyridinium chloride, 1-ethyl-3-methylpyridinium ethyl sulfate, 3-acetonylbenzyl-4-hydroxycoumarin, methyl-β-cyclodextrin, sodium salicylate, nonaethylene glycol (Polydocanol), 2-pyridinol-1-oxide (oxypyrion), ethylene carbonate, 2-methyl-4-isothiazolin-3-one, 1-butyl-3-methylimidazolium octylsulfate, 8-anilino-1-naphthalenesulfonic acid, acetonitrile, ethanol, methanol, 2-isopropanol, arachidonic acid, guanidine HCl, sodium dodecyl sulfate (SDS), Tween-20, CHAPS, EDTA, DTT, TCEP, Triton x-100, Zwittergent 3-14, Brij-35, NP-40 and protein (BSA, casein).

In addition, various types and concentrations of buffer salts (e.g., Tris, MES, citrate) were used in the dissociation buffers, assay buffers and wash buffers. Dissociation and wash buffers having a pH from 4-8 were tested. Dissocation was performed at different temperatures (RT, 37° C., 65° C.) and in different incubation vessels (polypropylene or polystyrene) and the competitive ELISA was performed using various different 25OHD conjugates.

Results

Of the dissociation buffer components (i.e., release reagents and associated compounds) tested to release 25OHD from DBP and maintain 25OHD availability for antibody binding, the following compounds were found to be effective and generally compatible with the assay: 1-butyl-4-methylpyridinium tetrafluoroborate, 1-butyl-3-methylimidazolium tetrafluoroborate, 1-butyl-4-methylpyridinium chloride, 1-ethyl-3-methylpyridinium ethyl sulfate, methyl-β-cyclodextrin, sodium salicylate, and 1-butyl-3-methylimidazolium octylsulfate. Methyl-β-cyclodextrin and sodium salicylate did not show a large effect towards dissociation of 25OHD from DBP in earlier experiments, but appeared to be effective in preventing 25OHD re-uptake by DBP or binding to other cellular proteins/lipids. See U.S. Pat. No. 7,087,395 (Garrity et al.).

Certain quaternary salts with tetrafluoroborate as the anion were found to be effective and compatible with the immunoassay when used as a component in the dissociation buffer when freshly made (i.e., reconstituted for less than 2 hours). These reagents became unstable over time, causing the pH of the dissociation buffer to decrease from 5.2 when freshly made, to 4.7 after 1.5 days, 4.07 after 4 days, 3.46 after 7 day, 2.79 after 8 days and 2.43 after 9 days, as is shown with 1-butyl-4-methylpyridinium tetrafluoroborate shown in FIG. 1. Thus, within 7 days after manufacture, a dissociation buffer containing 1-butyl-4-methylpyridinium tetrafluoroborate became unreliable. The inventors discovered that the same dissociation buffer where 1-butyl-4-methylpyridinium chloride and 1-ethyl-3-methylpyridinium ethyl sulfate were substituted for tetrafluoroborate containing quaternary salts was stable and could be stored at room temperature for weeks with no change in efficacy in the assay. Thus, 1-butyl-4-methylpyridinium chloride and 1-ethyl-3-methylpyridinium ethyl sulfate were found to be superior release reagents to 1-butyl-4-methylpyridinium tetrafluoroborate.

Acetonitrile, ethanol, methanol and 2-isopropanol were found to be ineffective release reagents at concentrations that were tolerable in the assay for an automated format. Use of these reagents at an effective concentration would require a centrifugation step to remove precipitate, which is undesirable for a high throughput assay format. Arachidonic acid, guanidine HCl, SDS, Tween-20, CHAPS, EDTA, DTT and TCEP did not aid in dissociating 25OHD from DBP. Triton X-100, Zwittergent 3-14, Brij-35 and NP-40 were not tolerated in the assay.

The presence of protein (BSA, casein) at or above 0.5% in the assay negatively impacted absorbance signal and dynamic signal range.

A pH of 5-5.5 was found to be optimal for both the dissociation buffer and the wash buffer. When the assay was performed outside this range, decreases in absorbance signal and in release of 25OHD from DBP were observed. One possible effect is on the kinetics of the conjugate/substrate color development. Additionally, an assay pH out of the optimal range could affect the binding between the monoclonal antibody and 25OHD. MES was found to be a better buffer salt than Tris or citrate in the dissociation buffer and the wash buffer for the effective pH range. Increases or decreases in salt concentrations had no profound effect on the assay.

The assay was equally effective when dissocation occurred at any of the three temperatures tested (room temperature, 37° C. and 65° C.).

Primary incubation of samples with dissociation buffer could be performed in a polypropylene plate and the solution could be transferred into the coated immunoassay plate described above or, preferably, samples could be mixed with dissociation buffer in wells of the coated polystyrene plate without negatively affecting the assay.

6.2. Example 2: Optimization of the ELISA

The optimum concentration for dissociation buffer components 1-butyl-4-methylpyridinium chloride, 1-ethyl-3-methylpyridinium ethyl sulfate, methyl-β-cyclodextrin, and sodium salicylate were determined as follows.

For release reagents 1-butyl-4-methylpyridinium chloride and 1-ethyl-3-methylpyridinium ethyl sulfate, dissociation buffers were prepared that only incorporated a single release reagent. Each buffer was diluted to provide dissociation buffers with multiple concentrations of a single release reagent. Concentration ranges varied for each release reagent: 6-14% 1-butyl-4-methylpyridinium chloride and 9-15% 1-ethyl-3-methylpyridinium ethyl sulfate. Samples of SeraCon (SeraCare Life Sciences, Milford Mass.) (a serum-like diluent) or human serum containing 20 or 40 ng/mL 25OHD$_3$ were treated with the various dissociation buffers and displacement of the alkaline phosphatase (AP)-conjugated 25OHD$_3$ bound to the anti-25OHD antibody was measured via immunoassay. From these data, amount of 25OHD released is determined for each release reagent percentage relative to the SeraCon control.

For methyl-β-cyclodextrin and sodium salicylate, dissociation buffers were prepared that incorporated one of these reagents in combination with 1-butyl-4-methylpyridinium chloride and 1-ethyl-3-methylpyridinium ethyl sulfate (concentrations determined from prior experiments). Each of these buffers was further diluted resulting in dissociation buffers with multiple concentrations of methyl-β-cyclodextrin (0.0005-0.5%) or sodium salicylate (0.05-8%). Control samples containing no 25OHD were treated with the various dissociation buffers and effects upon the optical density from substrate conversion were measured via immunoassay.

To test the effects of pH on assay performance, dissociation and assay buffers of varying pH (4-6, increments of 0.4 pH units) were prepared using a sodium citrate-based buffer for sample treatment and antibody and conjugate dilution. A standard curve of 25OHD$_3$ was analyzed along with the appropriate diluent control for each pH value being tested and the assay performed as described previously.

Results

Figure 2:
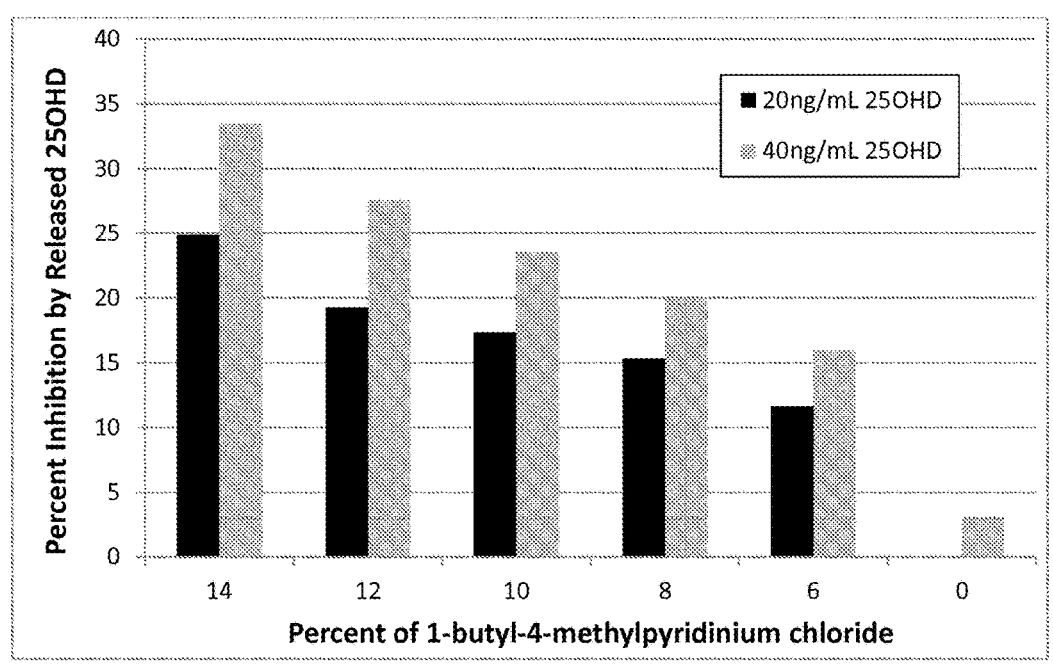

The effective concentrations of 1-butyl-4-methylpyridinium chloride and 1-ethyl-3-methylpyridinium ethyl sulfate in the dissociation buffer were determined by relative release of 25OHD$_3$ in two serum samples. As shown in FIG. 2, through the range of concentrations of 1-butyl-4-methylpyridinium chloride tested (6-14%) there was a gradual increase in percent inhibition by released 25OHD with a concomitant increase in percentage of 1-butyl-4-methylpyridinium chloride contained in the dissociation buffer. This trend was seen for both serum samples, with the 40 ng/mL sample showing a greater overall percent inhibition of released 25OHD at all 1-butyl-4-methylpyridinium chloride percentages tested (percent inhibition of released 25OHD from 12% increasing to 25% for the 20 ng/mL sample and 16% increasing to 34% for the 40 ng/mL sample as compared to controls with no 25OHD). While 1-butyl-4-methylpyridinium chloride does have a greater effect at higher concentrations on an individual basis, this comes at the expense of assay signal, decreasing the overall dynamic range of the substrate color development and therefore the sensitivity of the assay.

Figure 3:
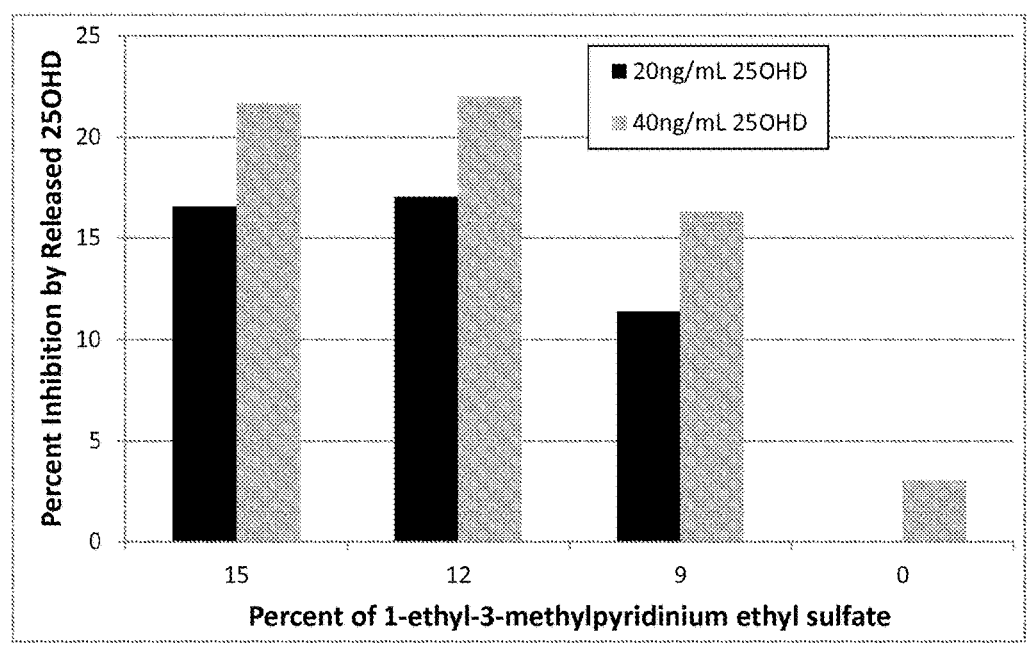

Similar testing was performed for 1-ethyl-3-methylpyridinium ethyl sulfate with concentrations tested ranging from 9-15%. The results of which are shown in FIG. 3. There was an increase in relative percent inhibition of released 25OHD when increasing the amount of 1-ethyl-3-methylpyridinium ethyl sulfate to 12%. Higher amounts of 1-ethyl-3-methylpyridinium ethyl sulfate did not seem to affect the percent inhibition by 25OHD, with 20 ng/mL samples showing 17% inhibition by released 25OHD and 40 ng/mL samples maintaining 22% inhibition as compared to controls with no 25OHD. As with 1-butyl-4-methylpyridinium chloride, testing with 1-ethyl-3-methylpyridinium ethyl sulfate also showed the same trend of the 40 ng/mL sample having a greater overall percent inhibition by released 25OHD at all percentages tested.

Figure 4:
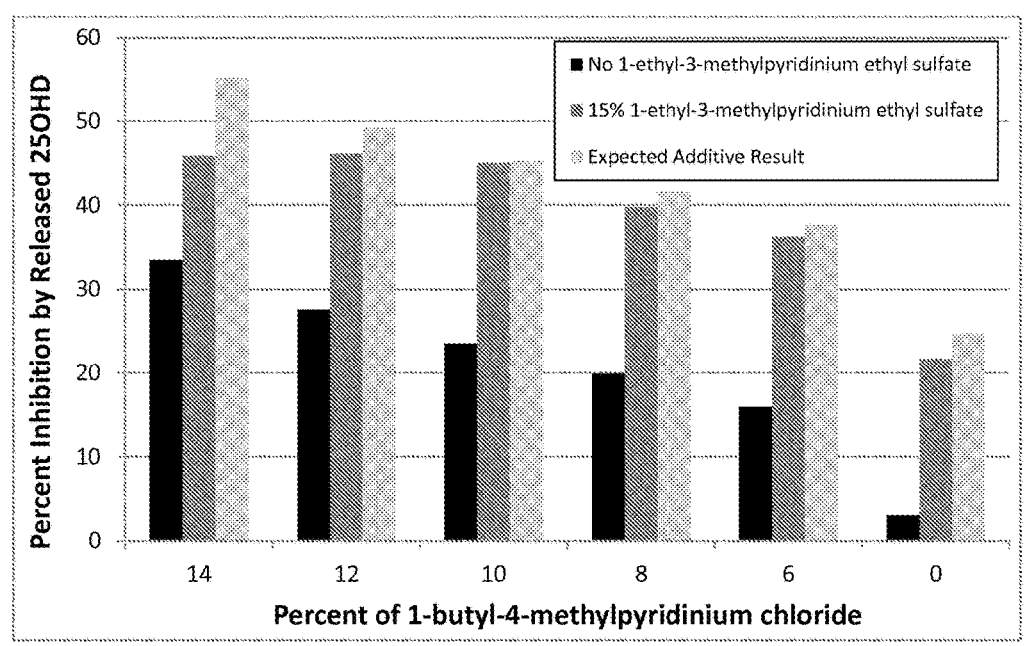

These results indicate that the best percentages of 1-butyl-4-methylpyridinium chloride and 1-ethyl-3-methylpyridinium ethyl sulfate are 14% and 12%, respectively, which are the concentrations of those individual release reagents that achieved the greatest gains in 25OHD release. To verify the performance of these concentrations, all concentrations of 1-butyl-4-methylpyridinium chloride and 1-ethyl-3-methylpyridinium ethyl sulfate used in the prior experiments were combined and tested for additive effects. When used in combination with 1-butyl-4-methylpyridinium chloride, 1-ethyl-3-methylpyridinium ethyl sulfate at the 15% concentration resulted in a greater amount of 25OHD released than when used at 12%. Also, when in combination, there were no additional positive effects gained with concentrations of 1-butyl-4-methylpyridinium chloride greater than 10%. In fact, as shown in FIG. 4, a comparison of expected additive effects of 1-butyl-4-methylpyridinium chloride across the range tested in combination with 1-ethyl-3-methylpyridinium ethyl sulfate at 15% showed that experimental results agree with expected results up to 1-butyl-4-methylpyridinium chloride at 10%. At greater amounts of 1-butyl-4-methylpyridinium chloride, actual release of 25OHD was less than the expected value based on experimentation with the individual components. Therefore optimal concentrations of the major release reagents for dissociation buffer formulation were determined to be about 10% 1-butyl-4-methylpyridinium chloride and about 15% 1-ethyl-3-methylpyridinium ethyl sulfate.

Figure 5:
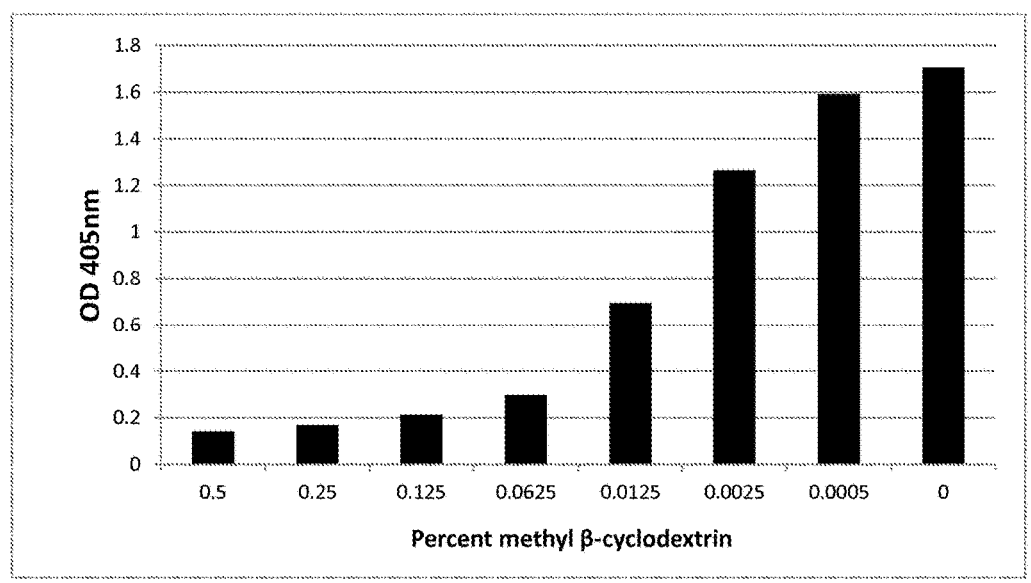
FIG. 5 shows the effect of various concentrations of methyl β-cyclodextrin on overall 25OHD immunoassay signal.

Non-interfering concentrations of the minor release reagent components of the dissociation buffer, methyl β-cyclodextrin and sodium salicylate, were determined by titration within the vitamin D immunoassay. Methyl β-cyclodextrin was tested across a range from 0.0005 to 0.5%. Results are shown in FIG. 5. This reagent showed detrimental effects to the assay signal at a concentration of 0.0125% and greater. Lower concentrations of methyl β-cyclodextrin also had some noticeable effect of decreasing the overall absorbance signal of the assay however these alterations did fall within the desired range for the assay signal. A final concentration of 0.001% methyl β-cyclodextrin was determined to be an effective concentration and optimal for assay signal.

Figure 6:
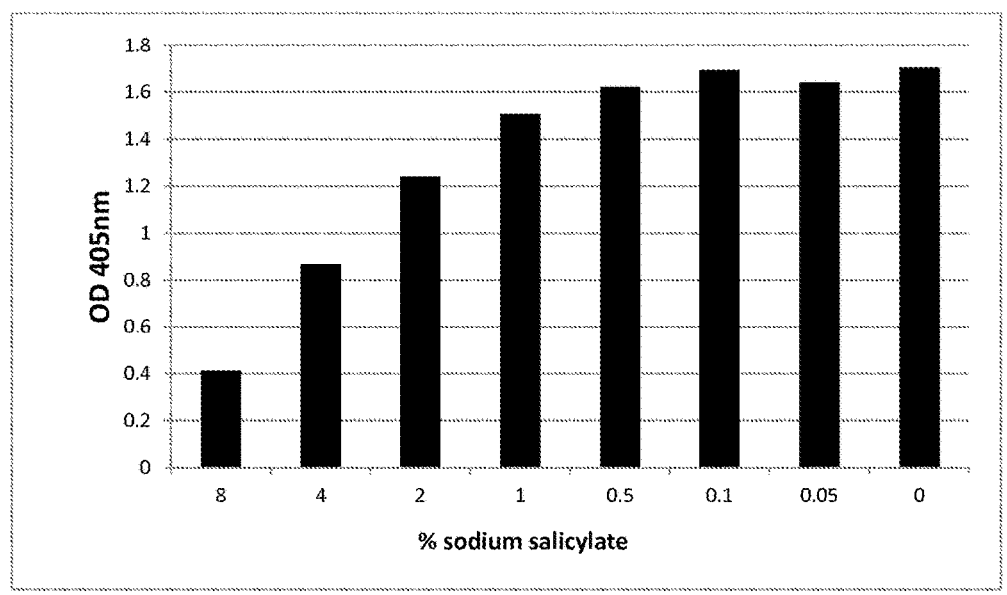
FIG. 6 shows the effect of various concentrations of sodium salicylate on overall 25OHD immunoassay signal.

Similar testing was performed for sodium salicylate with the concentration range that was tested being from 0.5 to 8% within the Vitamin D immunoassay. Results are shown in FIG. 6. This reagent was tolerated better by the assay than methyl β-cyclodextrin, with detrimental effects to signal arising at concentrations of 4% and above. Concentrations of 1-4% showed minor effects of decreasing signal of the assay and concentrations below 1% were very well tolerated. A final concentration of about 0.5% sodium salicylate was determined to be optimal for assay signal and inclusion in the dissociation buffer formulation.

The pH of the overall assay had an effect on the sensitivity of the assay itself. The optimal pH is defined as that which produces the lowest percent binding value for a given standard concentration which translates into the pH that has the highest assay sensitivity associated with it.

Figure 7:
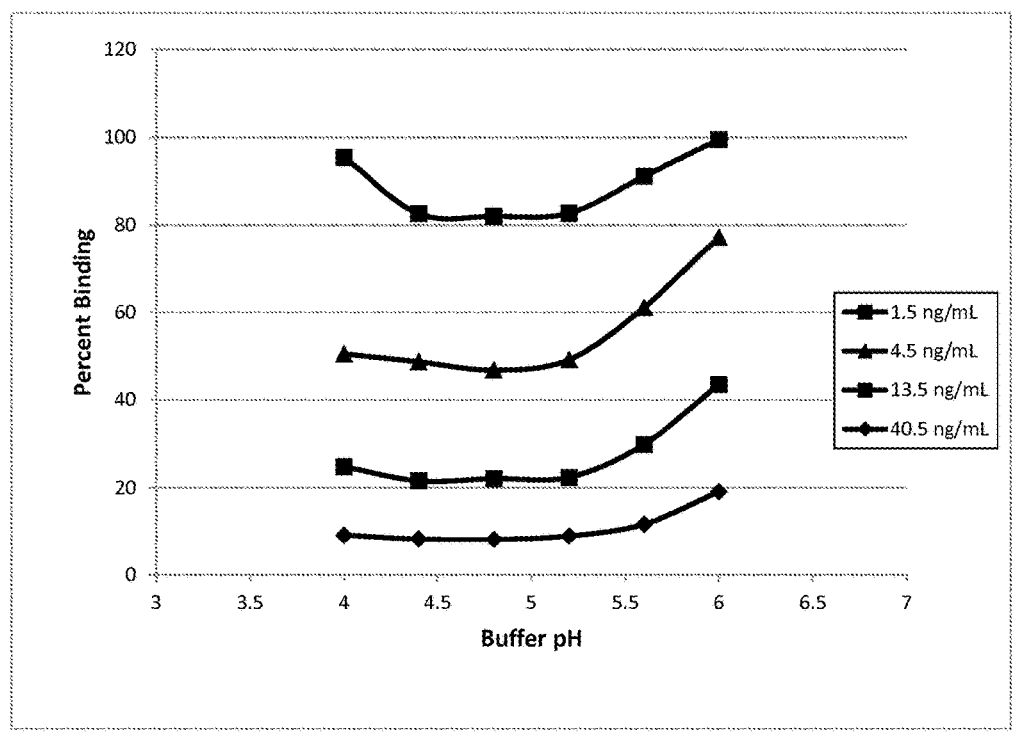
FIG. 7 shows the effect of pH on percent binding of a 25OHD conjugate to an anti-25OHD antibody for various concentrations of 25OHD$_3$ as noted in the figure. Each curve shows the effects that varying pH had on the binding in the presence of an amount of 25OHD.

As shown in FIG. 7, analysis of the percent binding for four concentrations of 25OHD tested within the linear portion of the standard curve reveals that the optimal pH for the assay is between 4.4 and 5.2. Prior experimentation had shown that MES was the optimal buffer to utilize in the 25OHD assay system, but in order to explore the effects of a wide range of pH values, a sodium citrate buffer was employed. Although this system returned lower overall optical density values, it was in agreement with previous testing showing that optimal pH was near a value of 5. In view of the buffering capacity and pH ranges of MES buffers as compared to citrate buffers, a pH of 5.2 was determined to be optimal for the 25OHD assay.

Suitable ranges for the major release reagents and the minor release reagents were determined to be from about 2.5% to about 20% of 1-butyl-4-methylpyridinium chloride; from about 1% to about 15% of 1-ethyl-3-methylpyridinium ethyl sulfate, from about 0.0005% to about 0.01% of methyl β-cyclodextrin, and from about 0.05% to about 4% of sodium salicylate.

Table 2 shows an optimized reagent makeup.

TABLE 2

Optimized ELISA Reagents

| Component | Concentration |
|---|---|
| Dilution Buffer pH 8 | |
| Tris HCl | 10 mM |
| BSA | 0.1% (w/v) |
| Zinc Sulfate | 0.1 mM |
| Magnesium chloride | 4.9 mM |
| Sodium azide | 0.09% (w/v) |
| Wash Buffer pH 5.2 | |
| MES (2-(N-morpholino)ethanesulfonic acid) | 50 mM |
| Sodium chloride | 100 mM |
| Polysorbate 20 (Tween-20) | 0.05% (v/v) |
| Kathon CG/ICP | 0.0025% (v/v) |
| Benzalkonium chloride | 0.000175% (v/v) |
| Dissociation Buffer pH 5.2 | |
| MES (2-(N-morpholino)ethanesulfonic acid) | 100 mM |
| Zinc Sulfate | 0.1 mM |
| Magnesium chloride | 4.9 mM |
| Sodium azide | 0.09% (w/v) |
| 1-butyl-4-methylpyridinium chloride | 10% |
| 1-ethyl-3-methylpyridinium ethyl sulfate | 15% |
| Methyl β-cyclodextrin | 0.001% |
| Sodium salicylate | 0.5% |

6.3. Example 3: Standard Curve Preparation

Six discrete standards were made for use in a standard curve for the measurement of 25OHD. The highest standard was prepared by dilution of a 1 mg/mL solution of 25OHD$_3$ with SeraCon Vitamin D depleted serum-like diluent (SeraCare Life Sciences, Milford Mass.). The remaining five standards were prepared by further diluting the highest standard with SeraCon Vitamin D depleted serum-like diluent to achieve the appropriate concentrations of the standard curve points.

6.4. Example 4: Preparation of Conjugate

The conjugate used in the ELISA described above was a 3-OH N-hydroxysuccinimide ester of 25OHD$_3$ conjugated to bovine intestinal alkaline phosphatase (AP). The conjugate was prepared as follows. 25(OH)VitaminD$_3$-NHS (Enzo Life Sciences, Farmingdale N.Y.) was resuspended in DMSO to a final concentration of 50 mg/mL immediately prior to use. A 10-fold molar excess of derivative was offered to AP in 50 mM borate buffer, pH 8.5. The conjugation was carried out in a glass vessel that had been placed inside a sealed jar containing desiccant. The solution was incubated for one hour at ambient temperature with constant stirring. Two additional aliquots ($2^{nd}$ and $3^{rd}$) of 25(OH)VitaminD$_3$-NHS were added (at a 10-fold molar excess to AP) to the conjugate mixture with one hour incubations between additions and under constant stirring. A $4^{th}$ aliquot of 25(OH)VitaminD$_3$-NHS (at a 10-fold molar excess to AP) was added to the mixture for a final molar offering of 40:1 (25(OH)VitaminD$_3$-NHS:AP). The solution was incubated overnight at 4° C. with constant stirring. The following day a PD-10 desalting column was conditioned with 2 column volumes of conditioning buffer (50 mM Tris, 150 mM NaCl, 0.1 mM ZnSO4, 4.9 mM MgCl$_2$, 0.1% BSA and 0.09% NaN$_3$, pH 7.5). To remove excess, unconjugated 25(OH)VitaminD$_3$-NHS, the conjugate mixture was added to the PD-10 desalting column and allowed to flow into the resin bed. Next, 5 mL of conditioning buffer was added to the column and 500 μL fractions were collected. Collected fractions were individually tested for AP activity. Fractions 5-8 were found to have the highest activity and were pooled. The conjugate solution was titered in the ELISA and found to have maximal performance at a 1:1000 dilution.

6.5. Example 5: Cross-Reactivity of Vitamin D Metabolites in the Assay

Ten vitamin D metabolites were tested for cross-reactivity in the optimized 25OHD ELISA assay described above. New concentrated stock solutions were prepared from dry chemicals for all metabolites. For cross-reactivity testing, each metabolite was prepared and serially diluted in a Tris buffer. Metabolites and the concentration ranges tested are in Table 3. The metabolite solutions were used as samples and mixed with dissociation buffer and the assay carried out as previously described.

TABLE 3

Vitamin D metabolites and concentration ranges tested for cross-reactivity in ELISA

| Vitamin D metabolite | Concentration range tested |
|---|---|
| 25(OH)VitaminD3 | 0.098-100 ng/mL |
| 25(OH)VitaminD2 | 0.098-100 ng/mL |
| 1,25(OH)$_2$VitaminD2 | 0.488-8000 ng/mL |
| 1,25(OH)$_2$VitaminD3 | 0.488-8000 ng/mL |
| 1α(OH)VitaminD2 | 0.488-8000 ng/mL |
| 1α(OH)VitaminD3 | 0.488-8000 ng/mL |
| 24,25(OH)$_2$VitaminD3 | 0.488-8000 ng/mL |
| 3-epi-25(OH)VitaminD3 | 0.488-8000 ng/mL |

TABLE 3-continued

Vitamin D metabolites and concentration ranges tested for cross-reactivity in ELISA

| Vitamin D metabolite | Concentration range tested |
|---|---|
| Vitamin D2 | 0.488-8000 ng/mL |
| Vitamin D3 | 0.488-8000 ng/mL |

Results

The percent cross-reactivity of each metabolite was determined at the OD corresponding to the ED50 of 25OHD$_3$. The results are shown in Table 4.

TABLE 4

Concentrations of calculated ED50 data and resulting calculated percent cross reactivity.

| Vitamin D metabolite | ED50 (ug/mL) | % cross-reactivity |
|---|---|---|
| 25(OH)VitaminD3 | 0.00175 | 100 |
| 25(OH)VitaminD2 | 0.00199 | 87.94 |
| 1,25(OH)$_2$VitaminD2 | 0.00186 | 94.1 |
| 1,25(OH)$_2$VitaminD3 | 0.00627 | 27.9 |
| 1α(OH)VitaminD2 | 1.43 | <0.01 |
| 1α(OH)VitaminD3 | 4.03 | 0.04 |
| 24,25(OH)$_2$VitaminD3 | 0.14 | 1.25 |
| 3-epi-25(OH)VitaminD3 | 0.00344 | 50.87 |
| Vitamin D2 | 1.643 | 0.11 |
| Vitamin D3 | 23.5 | 0.01 |

Cross-reactivity and detection of various metabolites by the anti-25OHD antibody was tested in the 25OHD assay. There is good equivalence for the detection of 25OHD$_3$ and 25OHD$_2$ (100 and 88% respectively). In this system, neither the parent vitamin compounds nor the 24,25(OH)$_2$VitaminD3 metabolite was detected to any appreciable degree. The metabolically active form 1,25(OH)$_2$D$_3$ and 1,25(OH)$_2$D$_2$ showed 28% and 94% cross reactivity respectively while the 3-epimer of 25(OH)VitaminD$_3$ had 51% cross reactivity.

The cross reactivity to the 1,25(OH)$_2$D$_3$ and 1,25(OH)$_2$D$_3$ metabolites should not be of major concern to the overall reported values of the 25OHD assay since the circulating level of these metabolites are approximately 1000-fold lower than circulating 25OHD levels (Ersfeld et al., 2004. Clin. Biochem. 37:867-874). Therefore, based on our measured cross-reactivity, concentrations of these metabolites at 10 times the normal concentration would contribute less than 0.5% to the overall 25OHD concentrations reported.

The 3-epi form of 25(OH)vitamin D results from the epimerization of the hydroxyl group at carbon 3 of the A-ring of the vitamin D molecule. Epimers of both 25OHD$_2$ and 25OHD$_3$ can be found in significant concentrations in young children that seems to be confined to infants less than one year old, attributing up to 60% of the overall reported 25OHD concentration (Singh et al., 2006. J. Clin. Endo. Metab. 91:3055-3061). Also, these epimers and those of the biologically active form 1,25(OH)$_2$D have been reported in several human and animal cell lines. However, like 1,25 (OH)$_2$D, the epimers are found in serum at concentrations between one and two orders of magnitude lower than the 25OHD metabolites. Considering the cross-reactivity reported above, this metabolite could contribute up to 5% of the overall reported concentration of 25OHD in the assay for infants up to 1 year of age. It should be noted that there is still debate as to the clinical significance of the C-3 epimers and their overall effective biological roles.

6.6. Example 6: Method Correlation of ELISA to LC-MS/MS

The immunoassay provided herewith was compared to an LC-MS/MS method. These methods were used to quantify total 25OHD levels, with the immunoassay detecting 25OHD$_2$ and 25OHD$_3$ with near equimolar affinity, and where levels reported of each analyte in LC-MS/MS can be used to determine total 25OHD.

A total of 193 serum samples were analyzed by the assays. The LC-MS/MS analysis was performed at Quest Diagnostics (Charter Township of Clinton, Mich.). The invention immunoassay was run as described previously and 25OHD concentrations of samples were calculated from a standard of 25OHD$_3$ prepared as discrete concentrations in SeraCon Vitamin D depleted diluent.

Figure 8:
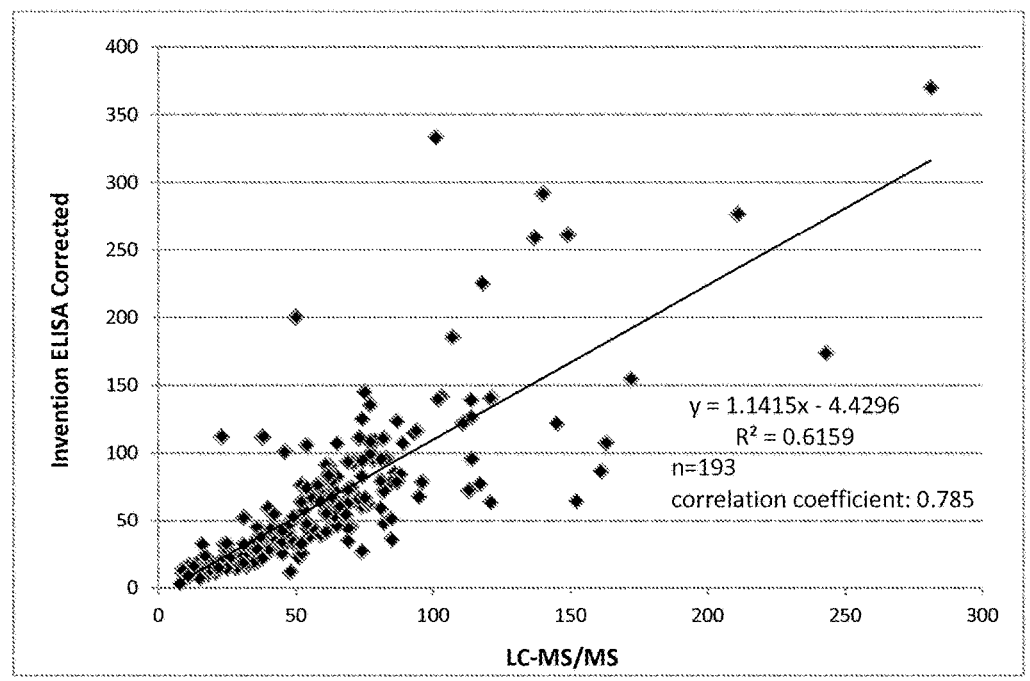
FIG. 8 shows a graph demonstrating the correlation between the invention immunoassay and an LC-MS/MS method for vitamin D quantitation for 193 serum samples.

Assigned concentrations for all samples were compared between the invention immunoassay and LC-MS/MS using a scatterplot to show the relationship between the described assay and LC-MS/MS. The data were analyzed by least squares regression and correlation coefficient was determined. For the 193 sample set, the method comparison was described with a linear regression slope of 1.14 and a correlation coefficient of 0.785. Results are shown in FIG. 8.

7. SPECIFIC EMBODIMENTS, CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A dissociation buffer comprising:
   1-ethyl-3-methylpyridinium ethyl sulfate at a concentration of 1% to 15%;
   1-butyl-4-methylpyridinium chloride at a concentration of 2.5% to 20%;
   methyl β-cyclodextrin at a concentration of 0.0005% to 0.01%; and
   sodium salicylate at a concentration of 0.05% to 4%, wherein the dissociation buffer is a 25-hydroxy vitamin D dissociation buffer.

2. The aqueous 25OHD dissociation buffer of claim 1, consisting essentially of:
   1-ethyl-3-methylpyridinium ethyl sulfate at a concentration of 1% to 15%;
   1-butyl-4-methylpyridinium chloride at a concentration of 2.5% to 20%;
   methyl β-cyclodextrin at a concentration of 0.0005% to 0.01%; and
   sodium salicylate at a concentration of 0.05% to 4%.

3. The dissociation buffer of claim 1, wherein
   the concentration of 1-ethyl-3-methylpyridinium ethyl sulfate is 15%, and
   the concentration of 1-butyl-4-methylpyridinium chloride is 10%.

4. The dissociation buffer of claim 1, comprising one or both of
   methyl β-cyclodextrin at a concentration of 0.001%, and
   sodium salicylate at a concentration of 0.05% to 1%.

5. The dissociation buffer of claim 4, further comprising:
2-(N-morpholino)ethanesulfonic acid;
zinc sulfate; and
magnesium chloride.

6. The dissociation buffer of claim 1, wherein
the concentration of methyl β-cyclodextrin is 0.001%, and
the concentration of sodium salicylate is 0.05% to 1%.

7. The dissociation buffer of claim 6, wherein the concentration of sodium salicylate is 0.5%.

8. The dissociation buffer of claim 2, consisting essentially of:
1-ethyl-3-methylpyridinium ethyl sulfate at a concentration of 15%;
1-butyl-4-methylpyridinium chloride at a concentration of 10%;
methyl β-cyclodextrin at a concentration of 0.0005% to 0.01%; and
sodium salicylate at a concentration of 0.05% to 4%.

9. The dissociation buffer of claim 8, wherein
the concentration of sodium salicylate is less than 1.0%.

10. The dissociation buffer of claim 9, wherein
the concentration of sodium salicylate is 0.5%.

11. A method for measuring 25-hydroxy vitamin D (25OHD) in a mammalian fluid sample comprising: a) contacting the mammalian fluid sample containing 25OHD with an antibody that specifically binds to 25OHD in the presence of a release reagent; and b) measuring the amount of 25OHD bound to the antibody, wherein the release reagent comprises 1-ethyl-3-methylpyridinium ethyl sulfate at a concentration of 1% to 15%;
1-butyl-4-methylpyridinium chloride at a concentration of 2.5% to 20%;
methyl β-cyclodextrin at a concentration of 0.0005% to 0.01%; and
sodium salicylate at a concentration of 0.05% to 4%, wherein the release reagent is a 25-hydroxy vitamin D dissociation buffer.

12. The method of claim 11, wherein the release reagent consists essentially of: 1-ethyl-3-methylpyridinium ethyl sulfate; 1-butyl-4-methylpyridinium chloride; methyl β-cyclodextrin; and sodium salicylate.

13. The method of claim 11, wherein the antibody is in solution.

14. The method of claim 11, in which the 25OHD is a conjugate, and which comprises before step (a) a step of binding said 25OHD conjugate to a surface.

15. The method of claim 11, which comprises after step (a) a step of binding 25OHD to a surface, wherein the 25OHD is bound to said surface by the antibody that specifically binds to 25OHD.

16. The method of claim 11, which comprises before step (a) a step of binding 25OHD to a surface, wherein the 25OHD is bound to said surface indirectly by an antibody that specifically recognizes the antibody that specifically binds to 25OHD.

17. The method of claim 11, wherein in step (a) said contacting is performed in the presence of add-in 25OHD bound to an enzyme.

18. The method of claim 11, which comprises after step (a) a step of adding add-in 25OHD bound to an enzyme to the mixture of step (a), wherein the action of the enzyme on a substrate bound to the antibody produces a signal that is measured in step (b), and wherein the signal measured in step (b) is inversely proportional to the amount of 25OHD in the sample.

19. The method of claim 11, which comprises after step (a) a step of adding add-in 25OHD bound to a substrate of an enzyme to the mixture of step (a), wherein the action of the enzyme bound to the antibody on the substrate produces a signal that is measured in step (b), and wherein the signal measured in step (b) is inversely proportional to the amount of 25OHD in the sample.

20. The method of claim 11, wherein the 25OHD is bound to an enzyme.

21. The method of claim 20, which comprises before step (b) a step of adding a substrate of said enzyme to the mixture of step (a), wherein the action of said enzyme on the substrate produces a signal that is measured in step (b).

22. The method of claim 11, wherein the 25OHD is bound to a substrate of an enzyme.

23. The method of claim 22, which comprises before step (b) a step of adding an enzyme to the mixture of step (a), wherein said enzyme recognizes the substrate bound to the 25OHD, and wherein the action of said enzyme on the substrate produces a signal that is measured in step (b).

24. The method of claim 11, wherein the antibody is bound to a surface.

25. The method of claim 24, wherein the antibody is bound to said surface directly.

26. The method of claim 24, wherein the antibody is bound to said surface indirectly.

27. The method of claim 26, wherein the antibody is bound to said surface by a secondary antibody that specifically binds to said antibody.

* * * * *